United States Patent [19]

Okaniwa et al.

[11] Patent Number: 4,567,136

[45] Date of Patent: Jan. 28, 1986

[54] ANALYTICAL ELEMENT

[75] Inventors: Kenichiro Okaniwa; Mikio Koyama; Shozo Kikugawa, all of Hino, Japan

[73] Assignee: Konishiroku Photo Industry Co., Ltd., Tokyo, Japan

[21] Appl. No.: 618,311

[22] Filed: Jun. 7, 1984

Related U.S. Application Data

[63] Continuation of Ser. No. 326,228, Dec. 1, 1981, abandoned.

[30] Foreign Application Priority Data

Dec. 4, 1980 [JP] Japan ................................ 55-171872

[51] Int. Cl.[4] .......................... C12Q 1/00; C12Q 1/28; G01N 21/78; G01N 33/52
[52] U.S. Cl. .......................................... 435/4; 422/56; 422/57; 435/28; 435/805
[58] Field of Search ................ 436/904, 66, 135, 95, 436/169, 170; 435/28, 805, 4; 422/56, 57; 430/552

[56] References Cited

U.S. PATENT DOCUMENTS

| | | | |
|---|---|---|---|
| 3,061,523 | 10/1962 | Free | 435/28 X |
| 3,616,251 | 10/1971 | Lecco et al. | 422/56 X |
| 3,703,375 | 11/1972 | Groet et al. | 430/552 X |
| 3,790,379 | 2/1974 | Oishi et al. | 430/552 X |
| 3,886,045 | 5/1975 | Meiattini | 435/28 X |
| 4,144,306 | 3/1979 | Figueras | 436/95 X |
| 4,260,679 | 4/1981 | Tsuda et al. | 435/28 X |

FOREIGN PATENT DOCUMENTS

| | | | |
|---|---|---|---|
| 0060693 | 5/1977 | Japan | 436/904 |
| 0045198 | 4/1981 | Japan | 435/28 |

OTHER PUBLICATIONS

"The Theory of the Photographic Process", (Third Edition), pp. 382–395, no publication date given.

*Primary Examiner*—Arnold Turk
*Attorney, Agent, or Firm*—Frishauf, Holtz, Goodman & Woodward

[57] ABSTRACT

There is disclosed an analytical element which comprises a support and a reagent layer comprising a peroxidative substance, a diffusion-resistant phenol compound, and an aromatic primary amine compound or its salt which brings about a coupling reaction with said diffusion-resistant phenol compound when oxidized, to thereby produce a dyestuff.

26 Claims, No Drawings

ANALYTICAL ELEMENT

This application is a continuation, of application Ser. No. 326,228, filed Dec. 1, 1981.

This invention relates to an analytical element, particularly to an analytical element useful for the detection of hydrogen peroxide or a substance generating hydrogen peroxide.

In the detection of a substance, which generates hydrogen peroxide in the presence of an enzyme and oxygen, such as cholesterol, uric acid and glucose, there has generally been used a method in which the hydrogen peroxide generated is detected.

As the above enzyme, glucose oxidase is used when the substance generating hydrogen peroxide is glucose, uricase when it is uric acid, or cholesterol oxidase when it is cholesterol.

As an analytical element for detection of a substance generating hydrogen peroxide, East German Pat. No. 135,243 discloses an element having a reagent layer on a support, said layer containing glucose oxidase, peroxidase, α-naphthol and N,N-dimethyl-p-phenylenediamine.

When a solution containing glucose is added dropwise on this analytical element, hydrogen peroxide is formed through the action of the glucose oxidase and N,N-dimethyl-p-phenylenediamine which has been oxidized with the resultant hydrogen peroxide in the presence of peroxidase having peroxidative activity further reacts with α-naphthol to form a dyestuff which can easily be detected.

However, the α-naphthol and the dyestuff formed from the α-naphthol and N,N-dimethyl-p-phenylenediamine as mentioned above are known to generally have a lower hydrophobic property. Thus, the α-naphthol and the dyestuff formed in the reagent layer, though the former is especially so, are under conditions freely migratable in the layer with water impregnated into the reagent layer. It has been known that by such an undesirable diffusion phenomenon, a localized high densification of the dyestuff formed, namely, a phenomenon called ringing is caused.

This ringing phenomenon, needless to say, leads to a noticeable judgement disturbance of the color density.

Also, in the enzyme test strip (or test strip) which is one embodiment disclosed in the same Patent, the dyestuff formed is disadvantageously low in hydrophobicity.

That is, the test strip which is an embodiment of the same Patent can be operated generally according to the Dip and read method in an analytical process. This method comprises dipping a test strip into a fluid sample and after impregnation with the liquid sample, and then removing it to read the color change. The aforesaid ringing phenomenon can also occur in this method, and flow-out of the reagent and the developed color dyestuff from the test strip leads to another problem.

The present inventors have made extensive studies to eliminate the drawbacks of analytical elements of the prior art for detection of hydrogen peroxide or a substance generating hydrogen peroxide.

That is, a first object of the present invention is to provide an analytical element for detection of hydrogen peroxide or a substance generating hydrogen peroxide.

A second object of the present invention is to provide an analytical element for quantitative determination of hydrogen peroxide or a substance generating hydrogen peroxide.

A third object of the present invention is to provide an analytical element in which no migration of the reagents and the dyestuff formed is caused.

The above objects and other objects hereinafter mentioned have been accomplished by use of an analytical element comprising a support and a reagent layer wherein said reagent comprises a substance having peroxidative activity, a diffusion-resistant phenol compound and an aromatic primary amine compound or its salt which can be oxidized to form a dyestuff through coupling reaction of the oxidized product with said diffusion-resistant phenol compound.

A diffusion-resistant phenol compound useful for the present invention possesses, on its benzene nucleus, a ballast group having a size and a steric configuration for permitting the phenol compound itself to keep in a diffusion-resistant state, the diffusion-resistant phenol compound being capable of forming a dyestuff by a coupling reaction with an oxidized product of an aromatic primary amine compound.

As the above-mentioned ballast group, an organic group having 8 or more carbon atoms is preferred, and a polymeric chain may also be included.

As the phenol compound mentioned above, there may be mentioned a compound having the ballast group on the benzene nucleus in which at least one of o-position and p-position relative to the hydroxyl group is not substituted or, when all of o-position and p-position have substituents, as least one of them is a group (hereinafter referred to as a split-off group) or an atom (hereinafter referred to as a split-off atom) which is capable of being split off on the coupling reaction of the phenol compound with an oxidized product of an aromatic primary amine compound.

Due to the presence of the ballast group, the phenol compound can be made diffusion-resistant to achieve the object of the present invention.

The ballast group can be the split-off group, and the dyestuff formed can be made smaller in diffusivity due to the increase in a molecular weight by the coupling reaction. However, in order to make the formed dyestuff sufficiently diffusion-resistant, it is particularly preferred that the ballast group is not the split-off group.

Among the phenol compounds, preferable compounds are those in which each p-position relative to a hydroxyl group is not substituted, or is substituted with a split-off group or atom, and which have each ballast group not being split-off by the coupling reaction on the benzene nucleus.

The diffusion-resistant phenol compounds which can be advantageously used in the present invention are represented by the following formula [I]:

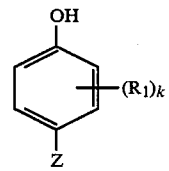

Formula [I]

wherein $R_1$ represents a mono-valent organic group or atom; Z a hydrogen atom, a split-off group or a split-off atom; k an integer of 0 to 4; at least one of $R_1$ and Z is a ballast group; when k is 2 to 4, each of $R_1$ may be either identical or different; and when two $R_1$'s are bonded at adjacent positions on the benzene ring, the two $R_1$'s may be bonded to each other to form a non-aromatic ring fused to the benzene ring.

As split-off atoms represented by Z, there may be mentioned halogen atoms such as a chlorine atom or a bromine atom.

As split-off groups represented by Z, there may be mentioned, for example, $-OR_2$, $-OCOR_2$, $-OSO_2R_2$, $-SR_2$, $-OCONHR_2$, $-OSO_2NHR_2$,

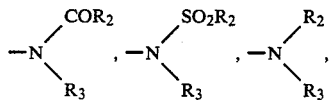

$-SCN$, etc. In the groups mentioned, $R_2$ and $R_3$ represent hydrogen atoms, aliphatic hydrocarbon residues, alicyclic compound residues, aryl groups or heterocyclic residues.

The atom represented by $R_1$ may be a halogen atom, for example, a chlorine atom or a bromine atom.

The mono-valent organic group represented by $R_1$ may include, for example, aliphatic hydrocarbon residues, alicyclic compound residues, heterocyclic residues, aryl groups, $-SCN$, $-OR_4$, $-OCOR_4$, $-OSO_2R_4$, $-SR_4$, $-OCONHR_4$, $-OSO_2NHR_4$,

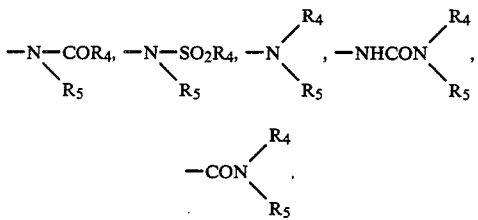

In the above formulae, $R_4$ and $R_5$ represent hydrogen atoms, aliphatic hydrocarbon residues, alicyclic compound residues, aryl groups or heterocyclic residues.

The aliphatic hydrocarbon residues represented by $R_1$, $R_2$, $R_3$, $R_4$ and $R_5$ may be either saturated or unsaturated and may also have either a straight chain or branched chain. They are preferably alkyl groups having 1 to 36 carbon atoms (e.g. methyl, ethyl, propyl, isopropyl, butyl, t-butyl, isobutyl, dodecyl, octadecyl) or alkenyl groups having 2 to 36 carbon atoms (e.g. allyl, octenyl).

The alicyclic compound residues represented by $R_1$, $R_2$, $R_3$, $R_4$ and $R_5$ may be 5- or 6-membered groups, for example, cyclopentyl and cyclohexyl.

Typical examples of heterocyclic residues represented by $R_1$, $R_2$, $R_3$, $R_4$ and $R_5$ may include, pyridinyl, pyrazinyl, pyridazinyl, quinolyl, pyrrolidyl, furalyl, thienyl, piperidyl, pyrolyl, pyrolinyl, tetrazolyl, thiadinyl, imidazolyl, morpholino, furyl, oxazolyl, thiazolyl, benzimidazolyl, benzoxazolyl, benzthiazolyl, etc.

The aryl groups represented by $R_1$, $R_2$, $R_3$, $R_4$ and $R_5$ may typically be phenyl and naphthyl.

As the non-aromatic ring fused to the benzene rings which are formed by the bond of the two $R_1$'s as mentioned above, may include 5- and 6-membered rings, for example, cyclopentane ring, cyclohexane ring and cyclohexene ring.

The aliphatic hydrocarbon residues, alicyclic compound residues, aryl groups and heterocyclic residues which are represented by $R_1$, $R_2$, $R_3$, $R_4$ and $R_5$, as well as the non-aromatic rings formed by the bond of the two $R_1$'s as mentioned above may include substituents.

As such substituents, there may be included, for example, halogen atoms (e.g. a chlorine atom and a fluorine atom), nitro group, cyano group, hydroxy group, keto group, carboxyl group, sulfo group, amino groups (e.g. amino, alkylamino, dialkylamino, anilino and N-alkylanilino), alkyl groups (e.g. methyl, propyl, isopropyl, t-butyl, octadecyl, cyanoalkyl, haloalkyl, aralkyl), alkenyl groups, aryl groups (e.g. phenyl, tolyl, acetylaminophenyl, 4-lauroylaminophenyl and ethoxyphenyl), heterocyclic residues, alkoxy groups (e.g. ethoxy, phenoxy, methoxy, tetradecyloxy), aryloxy groups (e.g. phenoxy, 2,4-di-t-amylphenoxy, p-t-butylphenoxy, 4-dodecyloxyphenoxy, 4-hydroxy-3-t-butylphenoxy, 4-hydroxy-3-n-butylphenoxy), arylthio groups, amide groups (e.g. acetamide, methanesulfonamide, p-dodecylbenzenesulfonamide), carbamoyl groups (e.g. N-p-carboxymethoxyphenylcarbamoyl, N,N-dihexylcarbamoyl, N-benzylcarbamoyl, N-ethylcarbamoyl, N-methoxyethylcarbamoyl), sulfamoyl groups (e.g. N,N-diethylsulfamoyl), alkyl sulfonyl groups, arylsulfonyl groups (e.g. benzensulfonyl, m-chlorobenzenesulfonyl), acyl groups (e.g. acetyl, p-chlorobenzoyl, benzoyl), acyloxy groups (e.g. acetyloxy, m-chlorobenzoyloxy), acyloxycarbonyl groups and alkoxycarbonyl groups (e.g. N-methoxyethylcarbamoylmethoxycarbonyl, ethoxycarbonyl, methoxycarbonyl, triethoxycarbonyl), aryloxycarbonyl groups (e.g. phenoxycarbonyl, p-nitrophenoxycarbonyl), arylthiocarbonyl groups (e.g. phenylthiocarbonyl), imide groups (succinimide, octadecylsuccinimide) and so on.

As another embodiment of the substituents, there may also mentioned groups containing a 1-hydroxyphenyl group.

As the ballast groups, those having 8 or more carbon atoms are preferred, which may be a polymeric chain, but they have generally 8 to 36 carbon atoms. In the formula [I], at least one of $R_1$ may preferably be a ballast group.

The integer k may preferably be 1 to 3.

Among the compounds [I] according to the present invention, preferred compounds are represented by the following formula [II]:

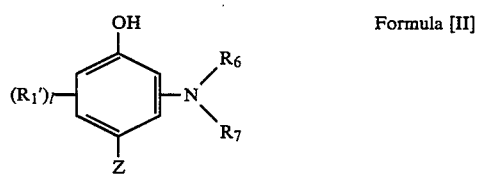

wherein $R_1'$ and $Z'$ have the same meanings as $R_1$ and Z in the formula [I], respectively, and include the same atoms and groups; $R_6$ represents a hydrogen atom, an aliphatic hydrocarbon residue, an alicyclic compound residue, an aryl group or a heterocyclic residue; $R_7$ an aliphatic hydrocarbon residue, an alicyclic compound residue, an aryl group, a heterocyclic residue, an acyl group, $-SO_2R_6'$ or a carbamoyl group; l is an integer of 0 to 3; when l is 2 or 3, each $R_1'$ may be identical or different; and at least one of $R_1'$, $Z'$ and

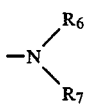

is a ballast group.

As $R_1'$, halogen atoms, alkyl groups having 1 to 36 carbon atoms, aryl groups having 6 to 16 carbon atoms, acyl groups having 2 to 36 carbon atoms,

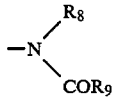

and $-SO_2R_9$ are preferred.

In the above formulae, $R_8$ represents a hydrogen atom or an alkyl group having 2 to 36 carbon atoms, and $R_6'$ and $R_9$ represent alkyl groups having 2 to 36 carbon atoms or aryl groups having 6 to 16 carbon atoms.

Among them $R_1'$ is preferably a halogen atom, an alkyl group or

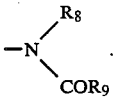

As said halogen atoms, a chlorine atom and a bromine atom are preferred.

As the alkyl groups represented by $R_1'$, $R_6'$, $R_8$ and $R_9$, there may be mentioned those represented by $R_1$ as set forth above. The alkyl group represented by $R_1'$ is preferred to have 1 to 8 carbon atoms (e.g. methyl, trifluoromethyl, difluorophenylmethyl), and especially methyl is preferred.

As $R_8$, a hydrogen atom or an alkyl group having 1 to 2 carbon atoms, especially a hydrogen atom or a methyl group, is preferred.

As aryl groups represented by $R_9$ and $R_6'$, there may be included those mentioned above for the aryl groups represented by $R_5$.

The above alkyl groups and aryl groups represented by $R_1'$, $R_6'$ and $R_9$ may have substituents, as exemplified by those mentioned above as the substituents for the alkyl groups and aryl groups represented by $R_1$, $R_2$, $R_3$, $R_4$ and $R_5$.

As $R_6$, a hydrogen atom or an alkyl group having 1 to 2 carbon atoms is preferred, and methyl is a preferable alkyl group.

As $R_7$, it is preferred to use a group represented by $-CO-R_{11}$ wherein $R_{11}$ is an alkyl group or an aryl group.

As the alkyl group and the aryl group represented by $R_{11}$, there may be included those as mentioned above for $R_4$, which may also have substituents. As such substituents, those mentioned with regard to the alkyl group and aryl group of $R_4$ may be included.

The group $Z'$ may preferably be a hydrogen atom, a halogen atom, $-O-R_{12}$ or $-O-CO-R_{13}$, wherein $R_{12}$ and $R_{13}$ represent an alkyl group having 2 to 36 carbon atoms or an aryl group having 6 to 16 carbon atoms. As said alkyl groups and aryl groups, there may be mentioned those as set forth above for $R_2$, which may also have substituents similar to those previously mentioned as substituents on $R_2$.

The integer l is preferred to be 0 to 2, especially 1 or 2.

The ballast group may preferably have 8 or more carbon atoms, including a polymeric chain, but usually has 8 to 36 carbon atoms.

In the formula [II], it is preferred that at least one of $R_1'$ and

should be a ballast group.

Typical examples of diffusion-resistant phenol compounds of this invention are shown below, but the compounds to be used in the present invention are not limited thereto.

Exemplary compounds (1-1) 2,4-dichloro-3-methyl-6-[α-(2,4-di-t-amylphenoxy)butylamido]phenol;

(1-2) 2-(α,α,β,β-tetrafluoropropionamido)-4-β-chloroethoxy-5-[α-(2,4-di-t-amylphenoxy)-butylamido]phenol;

(1-3) 2-chloro-3-methyl-4-ethylcarbamoylmethoxy-6-[α-(2,4-di-t-amylphenoxy)butylamido]phenol;

(1-4) 2-chloro-3-methyl-4-methoxycarbonylmethoxy-6-[α-(2,4-di-t-amylphenoxy)butylamido]phenol;

(1-5) 2-chloro-3-methyl-4-carboxymethoxy-6-[α-(2,4-di-t-amylphenoxy)butylamido]phenol;

(1-6) 2-chloro-3-methyl-4-(p-carbomethoxyphenylcarbamoylmethoxy)-6-[α-(2,4-di-t-amylphenoxy)-butylamido]phenol;

(1-7) 2-chloro-3-methyl-4-tri-ethoxycarbonylmethoxy-6-[α-(2,4-di-t-amylphenoxy)ethylamido]phenol;

(1-8) 2-chloro-3-methyl-4-methoxyethylaminocarbonylmethoxycarbonylmethoxy-6-[α-(2,4-di-t-amylphenoxy)butylamido]phenol;

(1-9) 2,4-dichloro-3-methyl-6-[3-(4-dodecylbenzenesulfonamido)benzamido]phenol;

(1-10) 2,4-dichloro-3-methyl-6-(ω-monohydrooctafluoropentanoylamino)phenol;

(1-11) 2,4-dibromo-3-methyl-6-(n-octadecanoylamino)-phenol;

(1-12) 2-(n-octylcarbonylamino)-4-chloro-5-[α-(2,4-di-t-amylphenoxy)ethylamido]phenol;

(1-13) 2-(ω-monohydro-octafluoropentanoylamino)-4-chloro-5-[α-(2,4-di-t-amylphenoxy)butylamido]-phenol;

(1-14) 2-(ω-monohydro-octafluoropentanoylamino)-4-chloro-5-[α-(2,4-di-t-amylphenoxy)-acetoamino]-phenol;

(1-15) 2-n-octafluorobutylcarbonylamino-5-[3-(3-n-pentadecanylphenoxy)propylcarbonylamino]-phenol;

(1-16) 2-n-octafluorobutylcarbonylamino-5-(2-n-lauryl-2-hydroxycarbonylethylcarbonylamino)-phenol;

(1-17) 2-(n-heptanylcarbonylamino)-5-[α-(2,4-di-t-amylphenoxy)butylamido]phenol;

(1-18) 2-(n-octafluorobutylcarbonylamino)-5-[α-(2,4-di-t-amylphenoxy)hexanoylamino]phenol;

(1-19) 2-(n-hexafluoropropylcarbonylamino)-5-[α-(2,4-di-t-amylphenoxy)pentylcarbonylamino]-phenol;

(1-20) 2-tetrafluoroethylcarbonylamino-5-[α-(2,4-di-t-amylphenoxy)propylcarbonylamino]phenol;

(1-21) 2-[α-(2,4-di-t-amylphenoxy)propylcarbonylamino-5-methyl]phenol;

(1-22) 2-[α-(2,4-di-t-amylphenoxy)propylcarbonylamino]phenol;

(1-23) 2-tetrafluoroethylcarbonylamino-5-methylphenol;

(1-24) 2-tetrafluoroethylcarbonylamino-5-n-pentadecanylphenol;

(1-25) 2-n-octafluorobutylcarbonylamino-5-[α-(2,4-di-t-amylphenoxy)methylcarbonylamino]phenol;

(1-26) 2-trifluoromethyl-6-n-undecanylcarbonylaminophenol;

(1-27) 2-phenyl-di-fluoromethyl-4-chloro-6-n-undecanylcarbonylaminophenol;

(1-28) 2-chloro-3-methyl-4-methanesulfonyloxy-6-(m-n-dodecanyloxyphenylcarbonylamino)phenol;

(1-29) 2-trifluoromethyl-4-methanesulfonylamido-6-(n-undecanylcarbonyl-N-methyl-amino)phenol;

(1-30) 2-chloro-3-methyl-4-(α-phenyl-α-carboxymethoxy)-6-[α-(2,4-di-t-butylphenoxy)butylamido]phenol;

(1-31) 2-chloro-3-methyl-4-n-octadecanyloxycarbonylmethoxy-6-phenylcarbonylaminophenol.

The diffusion-resistant phenol compounds to be used in the present invention are not limited to those as set forth above, but can be selected from compounds in great variety. Moreover, it is also possible to use two or more kinds of such compounds in combination.

The compounds of the present invention are generally oil-soluble and, a method for addition of the oil-soluble compounds is as follows: one or two or more kinds of the compounds according to the present invention are optionally dissolved in a solvent having a high boiling point of not less than 160° C. and/or a solvent having a low boiling point if desired, and are mixed with an aqueous solution containing a hydrophilic colloid such as gelatin containing an anionic surfactant and/or a nonionic surfactant, and the resultant mixture is dispersed into an emulsion by means of a high speed rotary mixer, a colloid mill or an ultrasonic dispersing means (this method is hereinafter referred to as Oil Protect Method).

As the solvent having a high boiling point, there may be mentioned, for example, organic acid amides, carbamates, esters, ketones, urea derivatives, more specifically di-n-butylphthalate, tricresyl phosphate, triphenyl phosphate, di-isooctyl acetate, di-n-butyl sebacate, tri-n-hexylphosphate, N,N-di-ethyl-caprylamidobutyl, N,N-di-ethyllaurylamide, n-pentadecylphenylether, dioctyl phthalate, n-nonyl phenol, 3-pentadecylphenylethylether, 2,5-di-sec-amylphenylbutylether, monophenyl-di-o-chlorophenyl phosphate or fluorinated paraffins. Among these, dialkyl phthalates, especially those having alkyl groups having 1 to 6 carbon atoms are preferred.

As the solvent having a low boiling point, there may be mentioned, for example, methyl acetate, ethyl acetate, propyl acetate, butyl acetate, butyl propionate, cyclohexanol, diethyleneglycol monoacetate, nitromethane, carbon tetrachloride, chloroform, cyclohexane, tetrahydrofuran, methyl alcohol, acetonitrile, dimethylformamide, dioxane, methyl ethyl ketone, etc.

Typical examples of anionic surfactants are alkylbenzene sulfonates and alkylnaphthalene sulfonates, while nonionic surfactants are typically sorbitane sesquioleate and sorbitane monolaurate.

As the aromatic primary amine compounds, o- or p-aminophenol series compounds and o- or p-phenylenediamine series compounds may be included. Preferably, o- or p-phenylenediamine series compounds, particularly p-phenylenediamine series compounds are preferred.

The p-phenylenediamine series compounds preferably used in the present invention are represented by the following formula [III]:

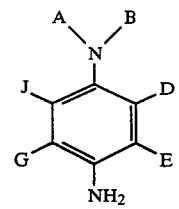

Formula [III]

wherein A and B represent hydrogen atoms or alkyl groups, and may form a heterocyclic ring together with a nitrogen atom; D, E, G and J represent hydrogen atoms, halogen atoms, hydroxy groups, amino groups, alkoxy groups, acylamide groups, arylsulfonamide groups, alkylsulfonamide groups or alkyl groups.

As the alkyl groups represented by A and B, those having 1 to 6 carbon atoms, especially 1 to 4 carbon atoms are preferred. For example, methyl, ethyl and butyl groups may be mentioned. These alkyl groups may have substituents, as exemplified by ureido groups, tetrahydrofuryl group, carboxyl group, methansulfonamide group, sulfo group, methoxy group, ethoxy group, methoxyethoxy group, methoxyethoxyethoxy group and methoxytetraethoxy group.

As D, G and J, hydrogen atoms, alkoxy groups, alkylsulfonamide groups and arylsulfonamide groups are preferred. More preferably, hydrogen atoms are employed. As the group E, it is preferred to use a hydrogen atom, an alkyl group or an acylamide group, more preferably an alkyl group having 1 to 3 carbon atoms, especially methyl. As the salts of the compounds represented by the formula [III], there may be included salts of organic or inorganic acids, such as p-toluenesulfonic acid, sulfonic acid, sulfinic acid, sulfuric acid ester, sulfamic acid, thiosulfuric S-ester, carboxylic acid, phosphoric acid ester, amidophosphoric acid, phosphoric acid, phosphorus acid ester, organic boron compounds, hydrochloric acid and sulfuric acid. In particular, p-toluenesulfonic acid salts, hydrochloric acid salts and sulfuric acid salts are preferred.

In the following, typical examples of aromatic primary amine compounds are shown, but the present invention is not limited thereto (2-1) N,N-diethyl-3-methyl-4-aminoaniline;

(2-2) N,N-diethyl-4-aminoaniline;

(2-3) N-carbamidomethyl-N-methyl-4-aminoaniline;

(2-4) N-carbamidomethyl-N-tetrahydrofuryl-3-methyl-4-aminoaniline;

(2-5) N-ethyl-N-carboxymethyl-3-methyl-4-aminoaniline;

(2-6) N-carbamidomethyl-N-ethyl-3-methyl-4-aminoaniline;

(2-7) N-ethyl-N-tetrahydrofuryl-3-methyl-4-aminophenol;

(2-8) 3-acetylamino-4-aminodimethylaniline;

(2-9) N-ethyl-N-β-methanesulfonamidoethyl-4-aminoaniline;

(2-10) N-ethyl-N-β-methanesulfonamidoethyl-3-methyl-4-aminoaniline;

(2-11) N-methyl-N-β-sulfoethyl-p-phenylenediamine;

(2-12) N-ethyl-N-methoxyethyl-3-methyl-4-aminoaniline;
(2-13) N-ethyl-N-[2-(2-methoxyethoxy)ethyl]-3-methyl-4-aminoaniline;
(2-14) N-ethyl-N-{2-[2-(2-methoxyethoxy)ethoxy]ethyl}-3-methyl-4-aminoaniline;
(2-15) N-ethyl-N-[2-{2-[[2-[2-(2-methoxyethoxy)ethoxy]]ethyl}ethyl]-3-methyl-4-aminoaniline;
(2-16) N,N-diethyl-3-methanesulfonamidoethyl-4-aminoaniline.

The salts of the compounds represented by the formula [III] are generally water-soluble and added as an aqueous solution or an aqueous buffer solution to the analytical element. A salt having smaller solubility product in water may also be dispersed according to the Oild Protect Method as described and added as a dispersion.

The reagent layer according to the present invention contains a diffusion-resistant phenol compound as described above, an aromatic primary amine compound or its salt and a peroxidative substance as the reagents which react with the component (substance to be detected) in a liquid sample to be analyzed to form dyestuffs. Through the action of the above-mentioned peroxidative substance, hydrogen peroxide oxidizes the aromatic primary amine compound according to the present invention. As a result, the oxidized product of aromatic primary amine compound formed undergoes coupling reaction with the diffusion-resistant phenol compound according to the present invention to produce a dyestuff.

As peroxidative substances, those known in the art are usable, but a typical example thereof is peroxidase, which is an enzyme for catalyzing the reaction where hydrogen peroxide oxidizes another substance. This peroxidase is a conjugated protein generally containing iron porphyrin and exists in horseradish, potato, sap of fig, turnip (vegetable peroxidase), milk (lactoperoxidase) and leukoxytes (verdoperoxidase), as well as in microorganisms, and it can be obtained by extraction or fermentation. It is also possible to use a synthetic peroxidase as disclosed in "Theorell & Maehly, Acta Chem. Second Vol. 4, pp. 422–434, 1950". In addition to peroxidase, there may also be employed in the present invention methemoglobin, oxyhemoglobin, hemoglobin, alkaline hematin, hemin and hemin derivatives.

As peroxidative substances other enzymes, for example, iron thiocyanate, iron stannate, ferrous ferrocyanate, chromic salts (e.g. potassium chromic sulfate) adsorbed on silica gel and the like are useful.

When the substance to be detected is a substance which generates hydrogen peroxide, the reagent layer peferably further contains a catalyst as an additional reagent which can act on the substance to be detected to generate hydrogen peroxide. Through the action of the catalyst and oxygen, hydrogen peroxide can be formed from the substance to be detected, and further a dyestuff is formed by the action of the substance having peroxidation, the aromatic primary amine compound and the diffusion-resistant phenol compound.

Typical catalysts for generation of hydrogen peroxide are oxidases (oxidation enzymes). As the oxidases, there may be mentioned various examples as shown below which can be used for the substance to be detected capable of generating hydrogen peroxide.

For example, they include glucose oxidase, uric acid oxidase (or uricase), glycerine acid oxidase, D-asparagic acid oxidase, D (or L)-amino acid oxidase, L-gulono-γ-lactone oxidase, L-sorbose oxidase, sarcosin oxidase, L-2-hydroxy acid oxidase, 6-hydroxy-D-nicotin oxidase, 6-hydroxyl-L-nicotin oxidase, pyridoxamine phosphate oxidase, pyridoxine oxidase, hexose oxidase, O-aminophenol oxidase, amine oxidase (containing pyridoxal or flavin), xanthin oxidase, alcohol oxidase, ethanolamine oxidase, $N^6$-methyl-L-lysine oxidase, α-glycerophosphate oxidase, cholesterol oxidase, phosphorous acid oxidase, etc.

The dyestuff formed in the present invention exhibits excellent spectral absorption characteristics thereof. That is, a test sample, for example, in case of human serum, has a great absorption generally between 400 to 520 nm. On the other hand, the dyestuff formed in the present invention has its primary visible absorption at 600 to 700 nm. Thus, the analytical element according to the present invention suffers from no interference by other components in the test solution, and it is also excellent in detection sensitivity.

The quantities of the diffusion-resistant phenol compound, the aromatic primary amine compound, the peroxidative substance according to the present invention, as well as the quantity of the oxidation enzyme optionally employed, cannot be unitarily determined, but they should be determined individually depending on the concentration range of the substance to be detected and the measurement range thereof. For example, it is meaningless to uniformly and equally determine uric acid occurring in a small amount and glucose occurring in a greater amount in a liquid sample of blood.

Further, the quantities are variable depending not only on the quantity in a liquid sample but also on the purpose of measurement. That is, in the case where a performance required for the analytical element may be at a level of qualitative or semi-quantitative analysis, the quantity is to be determined in accordance with such a prupose. On the other hand, for the purpose of quantitative test, the quantity and the ratio of ingredients to be added are to be determined more severely. In other words, the quantity of ingredients to be added should suitably be determined depending on the required performance of the analytical element, its purpose of use and the items of analysis.

The enzymes to be used in the reagent layer have individually different optimum pH's at which the reaction activity is at its maximum. For this reason, it is advantageous to adjust the reagent layer to the optimum pH with use of a buffer agent. When two or more kinds of enzymes are used, however, the optimum pH of each enzyme does not necessarily coincide with each other. In this case, it is possible to adapt the pH of a buffer agent to the desired conditions and other conditions. For example, the optimum pH of glucose oxidase is 5.6, while that of peroxidase 7.0, but when a serum is used as a fluid sample, it is possible to select a buffer agent of pH 4.5 to 6.0 in order to remove the influence by fluoride ions (derived from preservative) in the serum, so long as enzyme activity is not remarkably lowered thereby.

The above-mentioned various reagents are generally used in the state of a dispersion in a hydrophilic colloid which is employed as a binder. As the hydrophilic colloid, there may be mentioned gelatin, gelatin derivatives such as acid-treated gelatin, deionized gelatin and acylated gelatin, and polyvinyl alcohol. It is also possible to incorporate a synthetic polymer latex in a hydrophilic colloid substance. Such a latex may be used in an amount of about 10% to 70% based on the total solid content.

The analytical element according to the present invention consists essentially of a support and a reagent layer, and as the support, there may be employed a good liquid permeable or absorptive material and a liquid impermeable material, and the support may be either light transmissive or light non-transmissive. A typical example of a liquid absorptive material is paper. A liquid absorptive support can be impregnated with reagents to provide so called test strips or test papers.

That is, after the reagents according to the present invention have been dispersed in, for example, water, a support is dipped in this dispersion to be impregnated with said reagents, followed by being dried, whereby the element of this invention can be produced. The thus formed analytical element, if desired, may further be attached on a liquid impermeable support as described below for the purpose of convenience in handling.

When a liquid impermeable material is used as the support, the analytical element is generally prepared by providing a reagent layer of a hydrophilic collid on a support. As the liquid impermeable support, there may be employed a plate made of metal, glass, plastic or the like, but the plastic plate is usually used. Such plastic materials may include, for example, various polymer materials such as cellulose triacetate, polyethylene terephthalate, polycarbonate or polystyrene. The thickness of the support may freely be selected, but is typically about 50 microns to about 350 microns.

The reagent layer may be formed as a single layer in which all the reagents are contained, or may comprise divided plural layers each of which includes each reagent. The film thickness and the degree of permeability of the reagent layer are variable over wide ranges depending on practical uses. A dried film thickness of about $10\mu$ to $100\mu$ has been found to be useful. The degree of permeability, as represented in terms of a swelling degree, may advantageously be about 150% to about 500%, particularly about 200% to about 350%.

It is possible to apply various treatments between said support and the reagent layer to improve the adhesion of the reagent layer to the support. For example, one of such treatments is to apply a polymer for primer coating as an auxiliary layer.

On the reagent layer of the present invention, there may also be provided a reflection layer, a filtration layer and a development layer, if necessary. The development layer has the function for developing a fluid sample so as to be distributed evenly in the lateral direction, and for affording to the reagent layer a constant volume of the fluid sample per unit area. The filtration layer has the function to remove the components which interfere with the dyestuff forming reaction by filtration of a fluid sample. The reflection layer has the function to reflect the light transmitted through the support when carrying out spectral analysis of the dyestuff formed as background. When these three layers are to be provided, it is preferred to provide in the order of the reflection layer, the filtration layer and the development layer from the side of the support. Alternatively, it is also possible to use a single layer having two of the above-mentioned three functions and another layer having the other one function. A single layer having the three functions may also be available.

As the development layer, there may be mentioned, for example, a layer having diatomaceous earth dispersed in a binder such as cellulose acetate, a layer comprising a natural or a synthetic microcrystalline colloid product such as cellulose, and a layer containing inert spherical particles with uniform particle sizes such as glass beads.

As the layer having the functions as the filtration layer and the reflection layer, there may be mentioned a layer having titanium dioxide or barium sulfate dispersed in a binder such as cellulose acetate or gelatin.

As the layer having all the three functions as described above, there are non-fibrous porous medium layer, as disclosed in U.S. Pat. No. 3,992,158 and a fibrous porous medium layer, as disclosed in the specification of Japanese Patent Application No. 99,580/1979. As a concrete example of the non-porous medium layer, the so called brushed polymer layer is known, for example, a cellulose ester is dissolved in a suitable combination of solvents comprising a good solvent for the polymer having a low boiling point and a poor solvent for the polymer having a boiling point higher than the good solvent and is coated on a support, followed by phase separation, to form a porous cellulose film. Alternatively, in place of providing a coating of a brushed polymer layer, a thin layer of a microporous filtration film having the three functions as described above may be laminated on a support. As such microporous filtration films, there may be mentioned, for example, brushed polymers prepared from cellulose esters, which are commercially available as "Millipore" (trade name; produced by Millipore Corporation).

The aforesaid porous medium may preferably have a porosity of about 25% or higher, more preferably about 50% to 95%. The film thickness, which may suitably be selected within the range from about $30\mu$ to about $500\mu$, is preferably about $50\mu$ to about $300\mu$.

On the other hand, a fibrous porous medium layer may also advantageously be used. The fibrous herein means comprehensively the structure in which loose fibers, filaments or strands are three-dimensionally entangled with each other. Therefore, the pores in the fibrous porous medium mean the voids formed as the result of such three-dimensional entanglements of fibers. Examples of such materials are, for example, filtration papers, natural or synthetic unwoven fabrics, synthetic papers and synthetic fiber filter papers.

Ionic (anionic or cationic) or nonionic surfactants may also be incorporated effectively into such non-fibrous or fibrous porous medium layers.

The analytical element according to the present invention may also be combined with other layers, if desired. For example, a dialysis layer for removing the substances which affect undesirable effect on quantitative analysis reaction and a migration inhibition layer for inhibiting migration of a water-soluble reagent to the side of a development layer may be provided between the reagent layer and the development layer. As a dialysis layer, it is possible to use a material such as cellophane, while as a migration inhibition layer, there may be employed a mixture of a hydrophilic colloid substance and a polymer having quaternary ammonium salt such as poly(vinylbenzyltrialkylammonium-chloride). These layers or other layers can be combined with various layers as described above in various fashions, if desired.

For detection of hydrogen peroxide or a substance generating hydrogen peroxide by use of the analytical element of the present invention, the analytical element may be dipped into a fluid sample to be detected or a fluid sample is added dropwise onto the analytical element, and, after a certain period of time, a dyestuff formed is compared with standard color chart or standard color scale, or measured by a spectrophotometer to determine the components in a fluid sample. The above analytical element is especially advantageous primarily in the fields of qualitative analysis or semi-quantitative analysis.

The fluid samples applicable to the present analytical element may be biological and non-biological on condition that hydrogen peroxide or a compound generating hydrogen peroxide is contained therein. Typical examples are sera(including blood plasma and blood serum), lymph and urine. The quantity of a fluid sample, in case of a test strip, is arbitrary, subject to more than such a level as permits the sample to be sifficiently impregnated into the absorptive carrier containing the reagents. On the other hand, the quantity in case where a reagent layer is provided on a support may also freely be selected, but it may preferably be about 50 $\mu$l to 5 $\mu$l, more preferably about 20 $\mu$l to 5 $\mu$l. Usually, it is preferred to use about 10 $\mu$l of a fluid sample.

The present invention is further illustrated by the following Examples, by which the present invention is not limited at all.

EXAMPLE 1

After providing a reagent layer containing a diffusion-resistant phenol compound [Exemplary compound (1-1), (1-7), (1-9), (1-12) and (1-18)], an aromatic primary amine compound [Examplary compound (2-1)], peroxidase and gelatin by coating on a transparent poly(ethyleneterephthalate) film support having a thin tacky primer coating, a filter paper (No. 7: produced by Toyo Filter Paper Co.) is put on the reagent layer, followed by drying, to prepare Samples 1-5 of the analytical element for detection of hydrogen peroxide according to the present invention. For comparison, there was also prepared a sample similar to Sample 1 except that $\alpha$-naphthol was contained in place of the Exemplary compound (1-1) and N,N-dimethyl-p-phenylenediamine in place of the Exemplary compound (2-1) [Comparison-1]. The quantities of respective reagents and gelatin are shown in Table 1-1. The dispersion of the diffusion-resistant phenol compound was carried out as follows.

After each exemplary compound was dissolved in ethyl acetate and dibutyl phthalate, an aqueous solution of Alkanol XC (trade name: produced by Du Pont de Nemours & Corporation) and an aqueous gelatin solution were added to the solution to effect dispersion.

ter PDA-65 (produced by Konishiroku Photo Industry Co., Ltd.). The average values are listed in Table 1-2.

TABLE 1-2

| Sample | Difference in reflection density between central and peripheral portions | Density at central portion |
| --- | --- | --- |
| 1 | 0.011 | 0.71 |
| 2 | 0.011 | 0.68 |
| 3 | 0.010 | 0.69 |
| 4 | 0.011 | 0.70 |
| 5 | 0.012 | 0.81 |
| Comparison-1 | 0.102 | 0.38 |

As apparently seen from the above results, while an undesirable dyestuff localizing phenomenon called ringing is observed in the color developed spot of Comparison sample, uniform color formation is effected in the samples according to the present invention without ringing, and good coloration is exhibited for hydrogen peroxide as can be seen from the color formation density.

EXAMPLE 2

In Sample 1 of Example 1, Exemplary compounds (2-12) and (2-16) were used in place of the Exemplary compound (2-1), under otherwise the same conditions as in Example 1, to prepare Samples 6 and 7, respectively, and further the same procedures as in Example 1 were repeated. As the result, no ringing and migration of dyestuff to the filter paper layer were observed in any of these samples, similarly to Example 1, and a clear color developed spot was confirmed.

EXAMPLE 3

Similarly to Samples 1, 2, 3, 4, 5 in Example 1 and Comparison sample 1, except for adding 240 units of glucose oxidase to the reagent composition in Example 1, there were prepared Samples 8, 9, 10, 11, 12 and Comparison sample 2. On each of these samples were spotted 100 mg of a standard aqueous glucose solution and 10 $\mu$l of standard serum, and measurements were conducted similarly to Example 1. As the result, undesirable ringing was observed only in the Comparison sample, but substantially no such phenomenon observed in any of samples of the present invention. The samples according to the present invention were found to have excellent quantitative characteristics with uniform color developed spots and color development corresponding to glucose concentration.

TABLE 1-1

| | Quantity of reagents (per. dm$^2$) | | | | | |
| --- | --- | --- | --- | --- | --- | --- |
| Sample No. | Exemplary compound | Quantity | Exemplary compound | Quantity | Gelatin quantity | POD*3 quantity |
| 1 | (1 - 1) | 4.1 × 10$^{-5}$ mole | (2 - 1) | 4.1 × 10$^{-5}$ mole | 215 mg | 180 units |
| 2 | (1 - 7) | " | " | " | " | " |
| 3 | (1 - 9) | " | " | " | " | " |
| 4 | (1 - 12) | " | " | " | " | " |
| 5 | (1 - 18) | " | " | " | " | " |
| Comparison 1*1 | -naphthol | " | PPD*2 | " | " | " |

*1 disclosed in East German Patent No. 135243
*2 N,N—dimethyl-p-phenylenediamine
*3 peroxidase On each of these samples, 10 $\mu$l of an aqueous 0.02% hydrogen peroxide solution was spotted, and then the reflection density at the central portion and the peripheral portion of the color developed spot was measured ten times with red light by means of Sakuradensitome-

EXAMPLE 4

Similarly to Sample 8 in Example 3, the reagent layer according to the present invention was coated on a transparent poly(ethyleneterephthalate) film support, followed by drying, and thereafter a primer layer and then a diffusion layer were coated similarly to Example 1-4 disclosed in U.S. Pat. No. 4,098,574 to prepare Sample 13. After spotting an aqueous glucose solution on this Sample, the sample was stored at 37° C. for 7 minutes. Then, the reflection density was measured, whereby uniform color developed spot in proportion to the glucose concentration was confirmed.

We claim:

1. An analytical element for the detection of a substance which generates hydrogen peroxide upon reaction with an enzyme which comprises a support and a reagent layer comprising a peroxidative substance, a diffusion-resistant phenol compound having been oil-protected, and an aromatic primary amine compound or salt thereof, said aromatic primary amine compound being capable of being oxidized to form an oxidized product, said oxidized product being capable of undergoing a coupling reaction with said diffusion-resistant phenol compound, to thereby produce a diffusion-resistant dyestuff.

2. The analytical element of claim 1, wherein said aromatic primary amine compound is an o- or p-aminophenol compound or an o- or p-phenylenediamine compound.

3. The analytical element of claim 1, wherein said diffusion-resistant phenol compound is substituted on its benzene nucleus with a ballast group having a size and a steric configuration which permits the phenol compound to retain its diffusion-resistant state.

4. The analytical element of claim 3, wherein said diffusion-resistant phenol compound is unsubstituted in at least one of the o-position and p-position relative to the hydroxy group.

5. The analytical element of claim 4, wherein said diffusion-resistant phenol compound is selected from a compound of the formula:

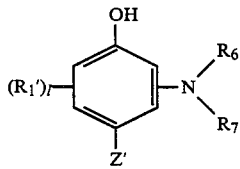

wherein $R_1'$ is a mono-valent organic group or atom; $Z'$ is a hydrogen atom, a split-off group or a split-off atom; $R_6$ is selected from the group consisting of a hydrogen atom, an aliphatic hydrocarbon residue, an alicyclic compound residue, an aryl group and a heterocyclic residue; $R_7$ is selected from the group consisting of an aliphatic hydrocarbon residue, an alicyclic compound residue, an aryl group, a heterocyclic residue, an acyl group, $—SO_2R_6'$, and a carbamoyl group, wherein $R_6'$ is an alkyl or aryl group; l is an integer of 0 to 3; when l is 2 or 3, each of $R_1'$ may be identical or different; and at least one of $R_1'$, $Z'$ and

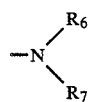

is a ballast group.

6. The analytical element of claim 5, wherein $R_1'$ is selected from the group consisting of a halogen atom, an alkyl group having 1 to 8 carbon atoms, an aryl group having 6 to 16 carbon atoms, an acyl group having 2 to 36 carbon atoms,

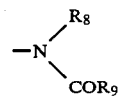

and $—SO_2R_9$, wherein $R_8$ is a hydrogen atom or an alkyl group having 2 to 36 carbon atoms, and $R_9$ is an alkyl group having 2 to 36 carbon atoms or an aryl group having 6 to 16 carbon atoms; $Z'$ is selected from the group consisting of a hydrogen atom, a halogen atom, $—O—R_{12}$ or $—O—CO—R_{13}$, wherein $R_{12}$ and $R_{13}$ are each an alkyl group having 2 to 36 carbon atoms or an aryl group having 6 to 16 carbon atoms.

7. The analytical element of claim 5, wherein said aliphatic hydrocarbon residue represented by $R_6$ or $R_7$ is an alkyl group having 2 to 36 carbon atoms or an alkenyl group having 2 to 36 carbon atoms; said alicyclic compound residue represented by $R_6$ or $R_7$ is a 6- or 6-membered group; said aryl group represented by $R_6$ or $R_7$ is a phenyl or naphthyl group; and said heterocyclic residue represented by $R_6$ or $R_7$ is selected from the group consisting of pyridinyl, pyrazinyl, pyridazinyl, quinolyl, pyrrolidyl, furalyl, thienyl, piperidyl, pyrolyl, pyrolinyl, tetrazolyl, thiadinyl, imidazolyl, morpholino, furyl, oxazolyl, thiazolyl, benzimidazolyl, benzoxazolyl and benzthiazolyl.

8. The analytical element of claim 4, wherein said diffusion-resistant phenol compound is selected from a compound having the formula:

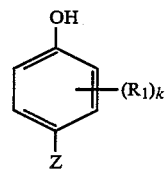

wherein $R_1$ is a mono-valent organic group or atom; $Z$ is a hydrogen atom or a group or an atom which is capable of being split off during said coupling reaction; k is an integer of 0 to 4 provided that at least one of $R_1$ and Z is a ballast group and when k is 2 to 4, each $R_1$ may be either identical or different; and when two $R_1$'s are attached at adjacent positions to the benzene ring, said $R_1$'s may be bonded to each other to form a non-aromatic ring fused to said benzene ring.

9. The analytical element of claim 8, wherein $R_1$ is selected from the group consisting of a halogen atom, an unsubstituted aliphatic hydrocarbon residue, a substituted aliphatic hydrocarbon residue, an unsubstituted alicyclic compound residue, a substituted alicyclic compound residue, an unsubstituted heterocyclic residue, a substituted heterocyclic residue, an unsubstituted aryl group, a substituted aryl group, a —SCN group, a $—OR_4$ group, a $—OCOR_4$ group, a $—OSO_2R_4$ group, a $—SR_4$ group, a $—OCONHR_4$ group, a $—OSO_2NHR_4$ group, a $—N(R_5)—COR_4$ group, a $—N(R_5)—SO_2R_4$ group, a $—N(R_5)R_4$ group,

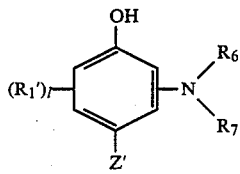

wherein $R_1$ is a mono-valent organic group or atom; $Z'$ is a hydrogen atom, a split-off group or a split-off atom; $R_6$ is selected from the group consisting of a hydrogen atom, an aliphatic hydrocarbon residue, an alicyclic compound residue, an aryl group and a heterocyclic residue; $R_7$ is selected from the group consisting of an aliphatic hydrocarbon residue, an alicyclic compound residue, an aryl group, a heterocyclic residue, an acyl group, $-SO_2R_6'$, and a carbamoyl group, wherein $R_6'$ is an alkyl or aryl group; $l$ is an integer of 0 to 3; when $l$ is 2 or 3, each of $R_1'$ may be identical or different; and at least one of $R_1'$, $Z'$ and

is a ballast group.

21. The analytical element of claim 20, wherein $R_1'$ is selected from the group consisting of a halogen atom, an alkyl group having 1 to 8 carbon atoms, an aryl group having 6 to 16 carbon atoms, an acyl group having 2 to 36 carbon atoms,

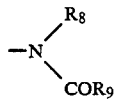

and $-SO_2R_9$, wherein $R_8$ is a hydrogen atom or an alkyl group having 2 to 36 carbon atoms, and $R_9$ is an alkyl group having 2 to 36 carbon atoms or an aryl group having 6 to 16 carbon atoms; $Z'$ is selected from the group consisting of a hydrogen atom, a halogen atom, $-O-R_{12}$ or $-O-CO-R_{13}$, wherein $R_{12}$ and $R_{13}$ are each an alkyl group having 2 to 36 carbon atoms or an aryl group having 6 to 16 carbon atoms.

22. The analytical element of claim 20, wherein said aliphatic hydrocarbon residue represented by $R_6$ or $R_7$ is an alkyl group having 2 to 36 carbon atoms or an alkenyl group having 2 to 36 carbon atoms; said alicyclic compound residue represented by $R_6$ or $R_7$ is a 5- or 6-membered group; said aryl group represented by $R_6$ or $R_7$ is a phenyl or naphthyl group; and said heterocyclic residue represented by $R_6$ or $R_7$ is selected from the group consisting of pyridinyl, pyrazinyl, pyridazinyl, quinolyl, pyrrolidyl, furalyl, thienyl, piperidyl, pyrolyl, pyrolinyl, tetrazolyl, thiadinyl, imidazolyl, morpholino, furyl, oxazoyl, thiazolyl, benzimidazolyl, benzoxazolyl and benzthiazolyl.

23. The analytical element of claim 19, wherein said diffusion-resistant phenol compound is selected from a compound having the formula:

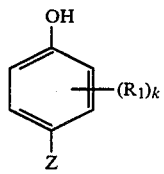

wherein $R_1$ is a mono-valent organic group or atom; $Z$ is a hydrogen atom or a group or an atom which is capable of being split off during said coupling reaction; $k$ is an integer of 0 to 4 provided that at least one of $R_1$ and $Z$ is a ballast group and when $k$ is 2 to 4, each $R_1$ may be either identical or different; and when two $R_1$'s are attached at adjacent positions to the benzene ring, said $R_1$'s may be bonded to each other to form a non-aromatic ring fused to said benzene ring.

24. The analytical element of claim 23, wherein $R_1$ is selected from the group consisting of a halogen atom, an unsubstituted aliphatic hydrocarbon residue, a substituted aliphatic hydrocarbon residue, an unsubstituted alicyclic compound residue, a substituted alicyclic compound residue, an unsubstituted heterocyclic residue, a substituted heterocyclic residue, an unsubstituted aryl group, a substituted aryl group, a $-SCN$ group, a $-OR_4$ group, a $-OCOR_4$ group, a $-OSO_2R_4$ group, a $-SR_4$ group, a $-OCONHR_4$ group, a $-OSO_2NHR_4$ group,

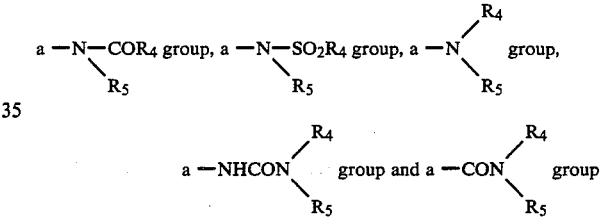

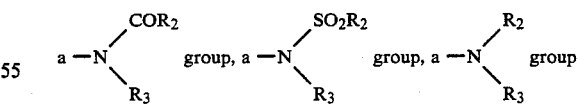

wherein $R_4$ and $R_5$ are each selected from the group consisting of a hydrogen atom, an unsubstituted aliphatic hydrocarbon residue, a substituted aliphatic hydrocarbon residue, an unsubstituted alicyclic compound residue, a substituted alicyclic compound residue, an unsubstituted aryl group, a substituted aryl group, an unsubstituted heterocyclic residue and a substituted heterocyclic residue; $Z$ is selected from the group consisting of a hydrogen atom, a halogen atom, a $-OR_2$ group, a $-OCOR_2$ group, a $-OSO_2R_2$ group, a $-SR_2$ group, a $-OCONHR_2$ group, a $-OSO_2NHR_2$ group, $$a-N\begin{matrix}COR_2\\R_3\end{matrix}\text{ group, } a-N\begin{matrix}SO_2R_2\\R_3\end{matrix}\text{ group, } a-N\begin{matrix}R_2\\R_3\end{matrix}\text{ group}$$

and a $-SCN$ group wherein $R_2$ and $R_3$ are each selected from the group consisting of a hydrogen atom, an unsubstituted aliphatic hydrocarbon residue, a substituted aliphatic hydrocarbon residue, an unsubstituted alicyclic compound residue, a substituted alicyclic compound residue, an unsubstituted aryl group, a substituted aryl group, an unsubstituted heterocyclic residue, a substituted hetercyclic residue; and said non-aromatic ring fused to the benzene ring which is formed by the bond of the two $R_1$ groups is selected from a 5- or 6-membered ring.

-continued

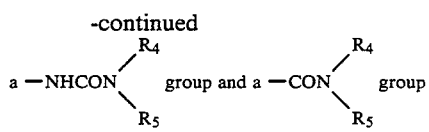

wherein R₄ and R₅ are each selected from the group consisting of a hydrogen atom, an unsubstituted aliphatic hydrocarbon residue, a substituted aliphatic hydrocarbon residue, an unsubstituted alicyclic compound residue, a substituted alicyclic compound residue, an unsubstituted aryl group, a substituted aryl group, an unsubstituted heterocyclic residue and a substituted heterocyclic residue; Z is selected from the group consisting of a hydrogen atom, a halogen atom, a —OR₂ group, a —OCOR₂ group, a —OSO₂R₂ group, a —SR₂ group, a —OCONHR₂ group, a —OSO₂NHR₂ group,

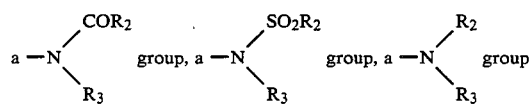

and a —SCN group wherein R₂ and R₃ are each selected from the group consisting of a hydrogen atom, an unsubstituted aliphatic hydrocarbon residue, a substituted aliphatic hydrocarbon residue, an unsubstituted alicyclic compound residue, a substituted alicyclic compound residue, an unsubstituted aryl group, a substituted aryl group, an unsubstituted heterocyclic residue, a substituted hetercyclic residue; and said non-aromatic ring fused to the benzene ring which is formed by the bond of the two R₁ groups is selected from a 5- or 6- membered ring.

10. The analytical element of claim 9, wherein said aliphatic hydrocarbon residue represented by R₁ to R₅ is an alkyl group having 1 to 36 carbon atoms or an alkenyl group having 1 to 36 carbon atoms; said alicyclic compound residue represented by R₁ to R₅ is a 5- or 6-membered group; said heterocyclic residue represented by R₁ to R₅ is selected from the group consisting of pyridinyl, pyrazinyl, pyridazinyl, quinolyl, pyrrolidyl, furalyl, thienyl, piperidyl, pyrolyl, pyrolinyl, tetrazolyl, thiadinyl, imidazolyl, morpholino, furyl, oxazoyl, thiazolyl, benzimidazolyl, benzoxazolyl and benzthiazolyl; and said aryl group represented by R₁ to R₃ is a phenol of naphthyl group.

11. The analytical element of claim 9, wherein the substituent or substituents on said aliphatic hydrocarbon residue, said alicyclic compound residue, said heterocyclic residue or said aryl group are selected from the group consisting of halogen atoms, nitro groups, cyano groups, hydroxy groups, keto groups, carboxyl groups, sulfo groups, amino groups, alkyl groups, alkenyl groups, aryl groups, heterocyclic residues, alkoxy groups, aryloxy groups, arylthio groups, amide groups, carbamoyl groups, sulfamoyl groups, alkylsulfonyl groups, arylsulfonyl groups, acyl groups, acyloxy groups, acyloxycarbonyl groups, alkoxycarbonyl groups, aryloxycarbonyl groups, and arylthiocarbonyl groups.

12. An analytical element for the detection of a substance which generates hydrogen peroxide upon reaction with an enzyme which comprises a support and a reagent layer comprising a peroxidative substance, a diffusion-resistant phenol compound having been oil-protected, and an aromatic primary amine compound or salt thereof, said aromatic primary amine compound being capable of being oxidized to form an oxidized product, said oxidized product being capable of undergoing a coupling reaction with said diffusion-resistant phenol compound, to thereby produce a diffusion-resistant dyestuff; said aromatic primary amine being a p-phenylenediamine selected from the compounds having the formula:

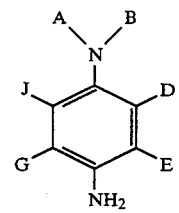

wherein A and B are each a hydrogen atom, an alkyl group or a substituted alkyl group, or together form a heterocyclic ring together with the nitrogen atom; D, E, G and J are each selected from the group consisting of hydrogen atoms, halogen atoms, hydroxy groups, amino groups, unsubstituted alkoxy groups, substituted alkoxy groups, unsubstituted acylamide groups, substituted acylamide groups, arylsulfonamide groups, unsubstituted alkylsulfonamide groups, substituted alkylsulfonamide groups and alkyl groups.

13. The analytical element of claim 12, wherein at least one of A and B is an alkyl group with is substituted with a substituent selected from the group consisting of a ureido group, a tetrahydrofuryl group, a carboxyl group, a methansulfonamide group, a sulfo group, a methoxy group, an ethoxy group, a methoxyethoxy group, a methoxyethoxyethoxy group and a methoxytetraethoxy group.

14. The analytical element of claim 12, wherein D, G and J are each selected from the group consisting of hydrogen atoms, alkoxy groups, alkylsulfonamide groups and arylsulfonamide groups.

15. The analytical element of claim 12, wherein E is a hydrogen atom, an alkyl group or an acylamide group.

16. The analytical element of claim 12, wherein the diffusion-resistant phenol compound is oil-protected in the presence of a solvent having a boiling point of at least 160° C.

17. The analyticl element of claim 12, wherein said diffusion-resistant phenol compound is substituted on its benzene nucleus with a ballast group having a side and a steric configuration which permits the phenol compound to retain its diffusion-resistant state.

18. The analytical element of claim 17, wherein said diffusion resistant phenol compound is substituted as the o-position or p-position relative to the hydroxy group with a substituent which is capable of being split off as a result of said coupling reaction.

19. The analytical element of claim 17, wherein said diffusion-resistant phenol compound is unsubstituted in at least one of the o-position and p-position relative to the hydroxy group.

20. The analytical element of claim 19, wherein said diffusion-resistant phenol compound is selected from a compound of the formula:

25. The analytical element of claim 24, wherein said aliphatic hydrocarbon residue represented by $R_1$ to $R_5$ is an alkyl group having 1 to 36 carbon atoms or an alkenyl group having 2 to 36 carbon atoms; said alicyclic compound residue represented by $R_1$ to $R_5$ is a 5- or 6-membered group; said heterocyclic residue represented by $R_1$ to $R_5$ is selected from the group consisting of pyridinyl, pyrazinyl, pyridazinyl, quinolyl, pyrrolidyl, furalyl, thienyl, piperidyl, pyrolyl, pyrolinyl, tetrazolyl, thiadinyl, imidazolyl, morpholino, furyl, oxazoyl, thiazolyl, benzimidazolyl, benzoxazolyl and benzthiazolyl; and said aryl group represented by $R_1$ to $R_5$ is a phenol or naphthyl group.

26. The analytical element of claim 24, wherein the substituent or substituents on said aliphatic hydrocarbon residue, said alicyclic compound residue, said heterocyclic residue or said aryl group are selected from the group, hydroxy groups, keto groups, carboxyl groups, sulfo groups, amino groups, alkyl groups, alkenyl groups, aryl groups, heterocyclic residues, alkoxy groups, aryloxy groups, arylthio groups, amide groups, carbamoyl groups, sulfamoyl groups, alkylsulfonyl groups, arylsulfonyl groups, acyl groups, acyloxy groups, acyloxycarbonyl groups, alkoxycarbonyl groups, aryloxycarbonyl groups, and arylthiocarbonyl groups.

* * * * *